United States Patent [19]
Donzier

[11] Patent Number: 5,956,132
[45] Date of Patent: Sep. 21, 1999

[54] METHOD AND APPARATUS FOR OPTICALLY DISCRIMINATING BETWEEN THE PHASES OF A THREE-PHASE FLUID

[75] Inventor: Eric Paul Donzier, Garches, France

[73] Assignee: Intellectual Property Law Dept. Schlumberger-Doll Research, Ridgefield, Conn.

[21] Appl. No.: 08/861,667

[22] Filed: May 22, 1997

[30] Foreign Application Priority Data

May 22, 1996 [FR] France ................................. 96 06361

[51] Int. Cl.⁶ ........................................................ G01N 21/41
[52] U.S. Cl. ........................ 356/133; 356/135; 356/136
[58] Field of Search .................................. 356/128, 133, 356/135, 136

[56] References Cited

FOREIGN PATENT DOCUMENTS

| | | |
|---|---|---|
| 0 194 732 | 9/1986 | European Pat. Off. . |
| 0 508 894 A1 | 10/1992 | European Pat. Off. . |
| 0 394 085 | 10/1990 | France . |
| 2 292 216 | 2/1996 | United Kingdom . |

*Primary Examiner*—Robert H. Kim
*Assistant Examiner*—Amanda Merlino
*Attorney, Agent, or Firm*—Keith Smith; David Garrod

[57] ABSTRACT

To discriminate optically between the various phases in a three-phase fluid, a light beam (F) of non-zero divergence is injected into a detector block (10) made of a material whose refractive index is greater than the refractive indices of all three phases of the fluid. The block (10) has a sensitive zone (18) and a total reflection zone (20) such that incident rays (Ri) parallel to the axis (12) of the block strike the sensitive zone (17) at an angle of incidence (Θi) and are returned parallel to the axis (12) by the total reflection zone (20). The angle of incidence (Θi) is such that a first phase gives rise to almost total reflection, a second phase gives rise to almost total transmission, and a third phase gives rise to partial transmission and partial reflection.

20 Claims, 4 Drawing Sheets

METHOD AND APPARATUS FOR OPTICALLY DISCRIMINATING BETWEEN THE PHASES OF A THREE-PHASE FLUID

BACKGROUND OF THE INVENTION

1. Field of the Invention

The invention relates to a method of optically discriminating between the phases of a moving three-phase fluid containing two first phases, e.g. liquid phases, of similar refractive indices, and a third phase, e.g., a gas phase, having a refractive index that is significantly different.

The invention also relates to apparatus for implementing the method.

The method and the apparatus of the invention can be used whenever it is desired to discriminate between the three phases of a moving fluid. A particular application lies in the oil industry, where it is common to find a single fluid coming from an underground deposit and comprising a mixture of liquid oil, of water, and of gas.

2. State of the Art

In the oil industry, it is essential to know as accurately as possible what fraction of the effluent from a well is constituted by liquid oil, and this applies both when testing and when producing from the deposit.

In practice, such knowledge is nevertheless very difficult to acquire accurately, particularly because the fluid extracted by a well generally contains three components (liquid oil mixed with water and with gas) which form three distinct phases above a certain depth.

Unfortunately, although various techniques exist that make it possible to distinguish between two phases contained in a fluid, the presence of three phases makes it necessary, at present, to use two detectors simultaneously. This gives rise to apparatus that is relatively complex and also provides a measurement of the oil fraction contained in the liquid which itself contains a relatively large amount of error. For example, one of the probes distinguishes the gas phase from the liquid phases while the other probe distinguishes between one of the liquid phases (generally water) and the other liquid phase and the gas phase taken together. The error inherent to the measurement is thus significantly increased when the fraction of oil present in the liquid is calculated on the basis of two measured fractions.

An illustration of the present state of the art is given by document EP-A-0 508 894 in which an optical probe and a radiofrequency probe are combined to form a single detector.

The presence of two different probes in a single detector also suffers from the drawback of inevitably situating the sensitive zones of the two probes in different locations. This is particularly true when the two probes are not integrated in a common detector, as is often the case. The sensitive zone of each of the probes can then be in the presence of a different phase of the fluid, such that interpreting results is particularly difficult. That constitutes another source of error which is additional to the preceding source of error in making measurements inaccurate.

In the particular case where phases are distinguished by means of an optical probe, the probe is generally constituted by the conical end of a silica optical fiber, as also shown in document EP-A-0 508 894. Given the refractive index of silica (about 1.46) and the refractive indices of gas (about 1) of water (about 1.33) and of liquid oil (about 1.5), the angle of the conical end is designed so that any incident light beam is reflected on the end surface of the fiber so long as said end surface is in gas, whereas on the contrary there is practically no reflection of the beam when the end surface of the fiber is in water or in liquid oil.

A conventional optical probe made in this manner thus provides good discrimination between gas and the liquid phases of the fluid, but it does not distinguish in any way between the liquid phases.

SUMMARY OF THE INVENTION

A particular object of the invention is to provide a method and apparatus enabling a single optical probe to discriminate directly between the three phases of a three-phase fluid such as a fluid containing a gas, water, and liquid oil. According to the invention, this result is obtained by means of a method of discriminating optically between the phases of a moving multiphase fluid capable of containing first and second phases having similar refractive indices and a third phase having a refractive index that is substantially different, the method comprising the steps of:

placing, in the fluid, a sensitive zone of a detector block made of a material having a refractive index greater than the refractive indices of the three phases of the fluid; and injecting an incident light beam into the block, the divergence of the beam being such that the fraction thereof reflected by the sensitive zone is respectively strong, medium, or weak, depending on which phase is in contact with the sensitive zone.

Here and throughout the present text, the terms "strong", "medium", and "weak" designate reflected fractions that do not overlap and, for example, are respectively greater than 70%, in the range 30% to 65%, and less than 20%.

A particular application concerns the case where the multiphase fluid contains water, oil, and gas, which have respective refractive indices of about 1.33, 1.5, and 1. Under such circumstances, the refractive index of the material from which the detector block is made is greater than 1.5.

In a preferred embodiment, where the refractive indices decrease from the first phase to the third phase, the method consists in:

placing in the fluid a sensitive zone and a total reflection zone that are adjacent and coaxial of a detector block made of a material having a refractive index greater than the indices of the three fluid phases, the sensitive zone and the total reflection zone forming respective first and second angles $\Theta 1$ and $\Theta 2$ relative to their common axis;

injecting into the block an incident light beam of non-zero divergence, centered on said common axis, the first and second angles $\Theta 1$ and $\Theta 2$ being such that rays of said beam that are initially parallel to the common axis strike the sensitive zone at least once at an angle of incidence $\Theta i$ intermediate between two limiting angles of reflection of the material as defined by the presence respectively of the first phase of the fluid and of the second phase of the fluid, and are reflected at least once by the total reflection zone to return in an opposite direction parallel to said common axis; and measuring a fraction of the incident beam as reflected by said zones, the relatively high, medium, or low measured value of the reflected fraction of the incident beam indicating respectively the presence of the third phase, of the second phase, and of the first phase of the fluid at the sensitive zone of the detector block.

According to the invention, the light path followed by the incident light beam is thus such that a central ray of the beam is incident at least once on the sensitive zone at the angle of incidence Θi. Given the particular value given to this angle of incidence Θi and the divergence of the incident light beam, while the sensitive zone is situated in the second phase, about half of the divergent incident light beam is reflected, whereas the fraction reflected is close to zero when the sensitive zone is in the first phase. Given that the sensitive zone also reflects practically all of the incident beam when said zone is in the third fluid phase, it is therefore possible to distinguish directly between the three fluid phases in a single operation.

It should be observed that this measurement is also made possible by the fact that the refractive index of the material from which the detector block is made is greater than the indices of all three phases of the fluid and by the fact that the angle Θ2 of the total reflection zone of said detector block ensures that the fraction of the light beam reflected by the sensitive zone returns parallel to the common axis of the two zones of the detector block. More precisely, the angles Θ1 and Θ2 formed by each of the two zones relative to their common axis are determined as a function of the refractive index of the material of the detector block so as to obtain the looked-for angle of incidence Θi and to ensure the return of the reflected fraction of the light beam after the incident beam has been incident on and reflected by each of the two zones at least once.

In the light path defined in this way, proper operation is ensured providing the optical axis of the beam intersects the sensitive zone at least once at the angle of incidence Θi and providing all of the other angles of incidence on any of the zones ensure total internal reflection of the beam regardless of the fluid phase in which the sensitive zone is immersed.

In a preferred implementation of the invention, in order to obtain a direct measurement of the fraction of the first fluid phase contained in the combination of the first and second phases taken together, independently of the fraction of the third phase contained in the fluid:

a measured reflected fraction is compared with a first threshold, intermediate between the medium reflected fraction and the relatively weak reflected fraction, to continuously issue a first binary signal representative of the first phase;

the measured reflected fraction is compared with a second threshold intermediate between the relatively strong reflected fraction and the medium reflected fraction to continuously issue a second binary signal whose zero level is representative of the third phase; and the mean of the product of the first and second binary signals is calculated which is representative of the proportion of the first phase in the first and second phases combined.

In a preferred implementation of the invention, the incident light beam injected into the detector block is caused to have non-zero divergence by connecting said detector block to an optical fiber having a numerical aperture that is not zero.

Advantageously, the material of the detector block is selected from a group comprising diamond and sapphire, given both the refractive indices of those materials and their good mechanical and chemical characteristics.

In a preferred application of the invention to discriminating between gas, water, and oil in a fluid, it is possible to use a diamond detector block having a central sensitive zone and a peripheral total reflection zone which form respective first and second angles Θ1 and Θ2 relative to their common axis such that the reflected fraction of the incident beam is subjected to reflection once only on the sensitive zone and once only on the total reflection zone (e.g. Θ1 is about 55° and Θ2 is about 35°).

In this same application, it is also possible to use a diamond detector block having a central sensitive zone and a peripheral total reflection zone which form respective first and second angles Θ1 and Θ2 relative to their common axis such that the reflected fraction of the incident beam is reflected once on the total reflection zone and twice on the sensitive zone (e.g. Θ1 is about 54.5° and Θ2 is about 19°).

Gas, water, and oil in a fluid can also be distinguished by using a sapphire detector block, having a central sensitive zone and a peripheral total reflection zone forming respective first and second angles Θ1 and Θ2 relative to their common axis such that the reflected fraction of the incident beam is subjected to two reflections on the total reflection zone and to two reflections on the sensitive zone (e.g. Θ1 is about 52° and Θ2 is about 7°).

In all cases, the sensitive zone of the detector block has a maximum diameter that, so far as possible, is no greater than the dimension of the smallest bubbles formed by the various phases of the fluid.

The invention also provides an apparatus for optically discriminating between the phases of a moving multiphase fluid, the fluid being capable of containing first and second phases having similar refractive indices and a third phase having a refractive index that is substantially different, the refractive indices decreasing from the first phase to the third phase, the apparatus being characterized by the fact that it comprises:

a detector block of material having a refractive index greater than the refractive indices of all three fluid phases, and including a sensitive zone; and means for injecting into the detector block an incident light beam of divergence such that the fraction reflected by the sensitive zone is respectively strong, medium, or weak, depending on which phase is in contact with the sensitive zone.

BRIEF DESCRIPTION OF THE DRAWINGS

Various implementations of the invention are described below by way of example with reference to the accompanying drawings, in which.

DESCRIPTION OF THE PREFERRED EMBODIMENTS

Figure 1:
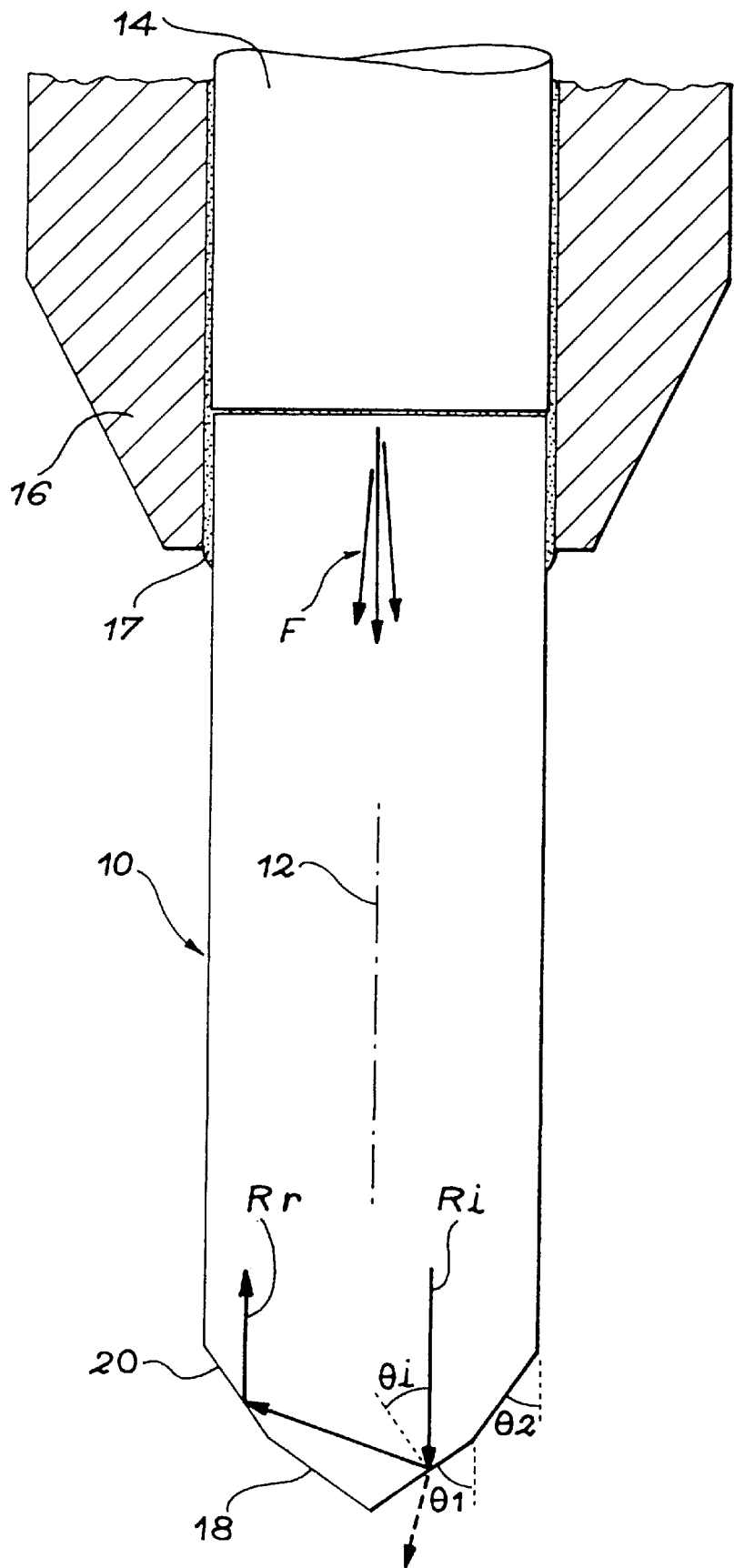
FIG. 1 is a longitudinal section view much greater than life size showing a first embodiment of a diamond detector block of the invention mounted at the end of an optical fiber and whose own end is shaped in such a manner that an incident light beam is reflected at least in part back into the optical fiber after striking both a sensitive zone and a total reflection zone.
Figure 2:
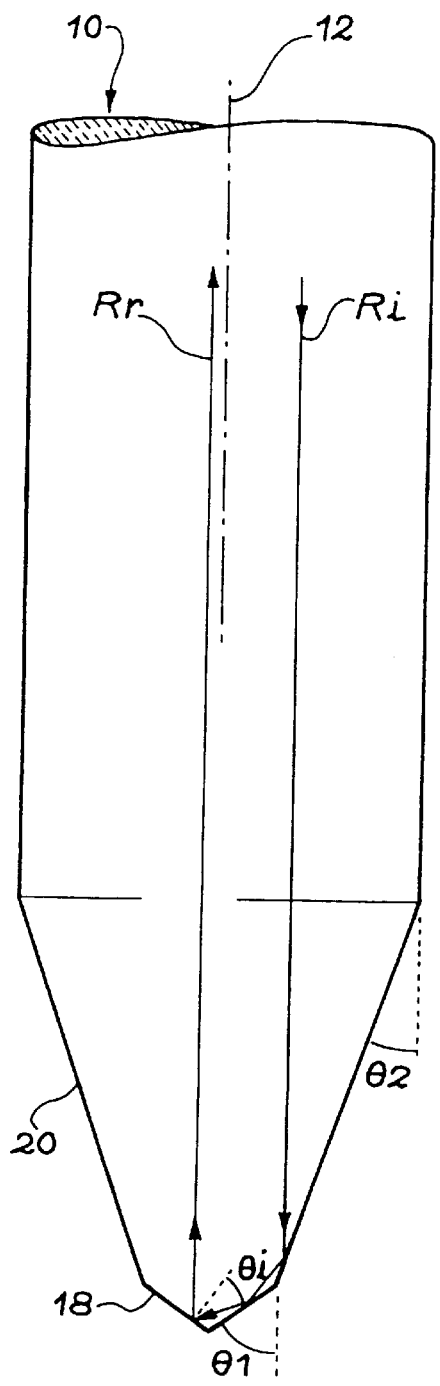
FIG. 2 is a view comparable to FIG. 1 showing in longitudinal section the end of a diamond detector block constituting a second embodiment of the invention, in which an incident light beam is reflected at least in part back into the optical fiber after striking a total reflection zone once and the sensitive zone twice.
Figure 3:
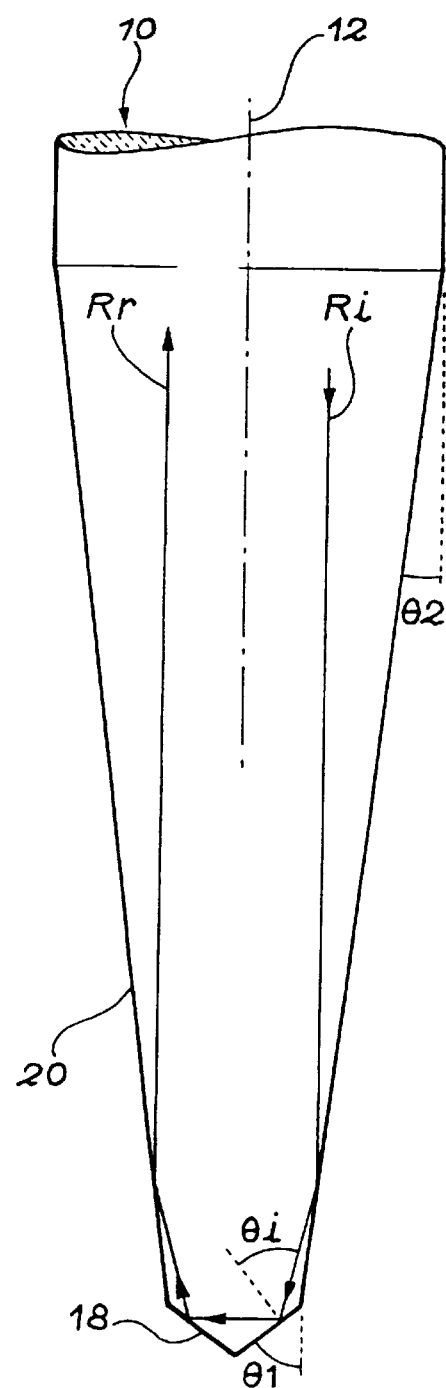
FIG. 3 is a longitudinal section comparable to FIGS. 1 and 2 showing a third embodiment of the invention in which the detector block is made of sapphire and has an end shaped in such a manner that an incident light beam is returned after striking the total reflection zone once, striking the sensitive zone twice, and striking the total reflection zone a second time.

FIGS. 1 to 3 show three different embodiments of a detector block 10 suitable for use in optical discriminator apparatus of the invention.

The detector block 10 is designed to be placed in a moving three-phase fluid so as to enable the three phases of the fluid to be distinguished optically in a single operation. More precisely, the invention applies to a moving three-phase fluid containing first and second phases that are generally liquid and of similar refractive indices n1 and n2, and a third phase, generally a gas, of refractive index n3 that is significantly different, the indices n1, n2, and n3 decreasing from the first phase to the third phase. As explained below, a particular application concerns a fluid whose two liquid phases are respectively water and oil.

The detector block 10 is made of a material capable of transmitting light rays well and having a refractive index n0 which is as high as possible so as to be greater than each of the indices n1, n2, and n3 of the three phases of the fluid. The material in which the detector block 10 is made may also be selected to take account of the environment in which it needs to be located when in use, e.g. the possibly corrosive nature of the environment. Finally, cost and ease of machining may also constitute criteria for selecting the material of the detector block.

In practice, the detector block 10 is advantageously made of sapphire, ruby, or diamond. In the embodiments shown in FIGS. 1 and 2, a detector block is used which is made of diamond, having a refractive index of about 2.4. In the embodiment of FIG. 3, the detector block 10 is made of sapphire, which has a refractive index of about 1.76.

The detector block 10 is constituted by a cylindrical bar (if made of sapphire) or a bar having facets (if made of diamond), presenting a longitudinal axis 12. The section of the bar may vary depending on the intended application. Nevertheless, this section is generally similar to that of the optical fiber 14 at the end of which the detector block 10 is mounted.

As shown in FIG. 1, the contacting end faces of the optical fiber 14 and of the detector block 10 are generally plane and extend radially relative to the longitudinal axis 12. As explained below, other configurations are nevertheless possible, without going beyond the ambit of the invention.

The detector block 10 may be mounted at the end of the optical fiber 14 by means of a metal tube 16, e.g. made of stainless steel. More precisely, the adjacent ends of the detector block 10 and of the optical fiber 14 are then stuck together and also to the tube 16 by means of a film of adhesive 17.

In the three embodiments of the invention shown in FIGS. 1 to 3, the end of the detector block 10 facing away from the optical fiber 14 is in the form of a biconical point centered on the longitudinal axis 12. More precisely, this end has a sensitive end zone 18 in the form of a cone which is at angle $\Theta 1$ relative to the axis 12, and a total reflection zone 20 adjacent to the sensitive zone 18 and in the form of a truncated cone which is at an angle $\Theta 2$ to the axis 12. The axis 12 thus constitutes a common axis to both zones 18 and 20.

It should be observed that the conical and frustoconical shapes of the zones 18 and 20 may be continuous or they may be constituted by facets, particularly when the detector block 10 is made of diamond.

In all cases, the angle $\Theta 1$ formed between the sensitive zone 18 and the axis 12 is greater than the angle $\Theta 2$ formed between the total reflection zone 20 and the same axis 12.

In the embodiment shown in FIG. 1, the angle $\Theta 1$ is determined so that incident light rays such as ray Ri travelling parallel to the axis 12 reach the sensitive zone 18 directly at a well-determined angle of incidence $\Theta i$.

More precisely, this angle of incidence qi is selected by taking account of the refractive index n0 of the material from which the detector block 10 is made, so as to have a value intermediate between the limiting angle of reflection for the material under consideration when in contact with the first liquid phase of the fluid of refracting index n1 and the limiting angle of reflection of the same material when in contact with the second liquid phase of the fluid of refractive index n2.

Thus, in the embodiment shown in FIG. 1, where the detector block 10 is made of diamond and is applied to discriminating between liquid oil, water, and gas, having average refractive indices respectively of about 1.5, about 1.33, and about 1, the corresponding limiting reflection angles in liquid oil and in water are respectively 38° and 33°. The angle of incidence $\Theta i$ is then given an intermediate value, e.g. 35°.

In the embodiment of FIG. 1, this value $\Theta i$ of angle of incidence serves to calculate directly the value of the angle $\Theta 1$ formed by the sensitive zone 18 relative to the axis 12. In this case, the angle $\Theta 1$ is 55°.

The angle $\Theta 2$ formed between the total reflection zone 20 and the longitudinal axis 12 is then determined so that the fractions of the incident rays Ri parallel to the axis 12 and reflected by the sensitive zone 18 strike the total reflection zone 20 at an angle of incidence such that said fractions are totally reflected on said zone 20 and returned to the optical fiber 14 parallel to the axis 12, as represented by ray Rr in FIG. 1.

Given the numerical values for the angle $\Theta i$ (35°) and the angle $\Theta 1$ (55°) given above, this means the angle $\Theta 2$ should have a value of 35° in the embodiment of FIG. 1.

It should be observed that the values of the angles $\Theta 1$ and $\Theta 2$ as determined in this way enable incident rays which are reflected firstly on the total reflection zone 20 to strike the sensitive zone 18 at the same angle of incidence $\Theta i$ following a path that is reversed relative to that followed by the rays Ri and Rr in FIG. 1.

In order to ensure that the apparatus has a response that is as accurate as possible, the zone 18 should be such as to be incapable of being in contact simultaneously with a plurality of phases of the fluid, apart from periods of transition between two phases. For this purpose, the sensitive zone 18 preferably has a maximum diameter that is no greater than the smallest dimension of bubbles formed by the various phases of the fluid in which detection is performed. In practice, this means that the maximum diameter given to the sensitive zone 18 should be less than 100 µm. Also, and solely by way of example, the diameter of the detector block 10 may be three times that of the sensitive zone 18.

In order to enable the apparatus to distinguish between the three phases of the fluid in which the sensitive zone 18 is immersed, a light beam is injected into the detector block 10 via the optical fiber 14 such that the divergence of the beam is non-zero, as represented by the arrows F in FIG. 1. The beam F of non-zero divergence and centered on the longitudinal axis 12 may be obtained, in particular, by using an optical fiber 14 which itself has an appropriate numerical aperture (non-zero).

The influence of the divergence of the light beam on the ability to distinguish between the three phases of the fluid is explained below with reference to FIG. 4.

The figure shows how the reflected fraction (in %) of the incident light beam varies as a function of the refractive index n of the phase of the fluid in which the sensitive zone 18 is immersed. It can be seen that the reflected fraction of the beam passes from a value close to 100% to a value close to zero as the refractive index increases. The slope in the intermediate region of the curve in which the reflected fraction diminishes progressively is a direct function of the divergence of the incident beam. More precisely, the slope of this intermediate region increases as the divergence of the beam decreases, and vice versa. By giving this slope an intermediate value, as shown in FIG. 4, it will be understood that the reflected fraction of the incident beam can be used to distinguish a phase whose refractive index is intermediate (zone A2) between a phase of higher index (zone A3) and a phase of lower index (zone A1).

When the divergence of the incident beam is obtained by using an optical fiber 14 of appropriate numerical aperture, it is possible to give said numerical aperture a value that is close to 0.22, for example.

In a variant, the non-zero divergence of the incident light beam may be obtained by interposing an optical device such as a lens between the facing ends of the optical fiber and the detector block 10, or by giving said ends a spherical shape that enables the desired beam divergence to be obtained.

Because of the divergence of the incident beam, the incident rays that reach the sensitive zone 18 directly form an angle of incidence relative thereto which may be slightly less than or slightly greater than the mean angle of incidence $\Theta i$ selected for incident rays Ri travelling parallel to the axis 12. Given the choice of angle $\Theta i$ as described above, this has the consequence that nearly all of the rays of the incident beam are transmitted by the sensitive zone 18 when it is immersed in the first phase of the fluid having the highest refractive index, i.e. in liquid oil in the application under consideration. In contrast, when the incident light beam reaches the sensitive zone 18 while it is immersed in the second phase of the fluid, having the intermediate refractive index, i.e. water in the application under consideration, fractions of substantially equal magnitude are respectively transmitted and reflected by said sensitive zone. Finally, when the sensitive zone is immersed in the third fluid phase, of smallest refractive index, i.e. gas in the application under consideration, practically all of the incident light beam is reflected by said sensitive zone.

Given that the reflected fractions of the incident light beam are returned in full towards the optical fiber by the total reflection zone 20, it is thus possible to distinguish between the three fluid phases depending on whether the reflected fraction is very weak (in the presence of liquid oil), medium (in the presence of water), or very strong (presence of gas).

Figure 4:
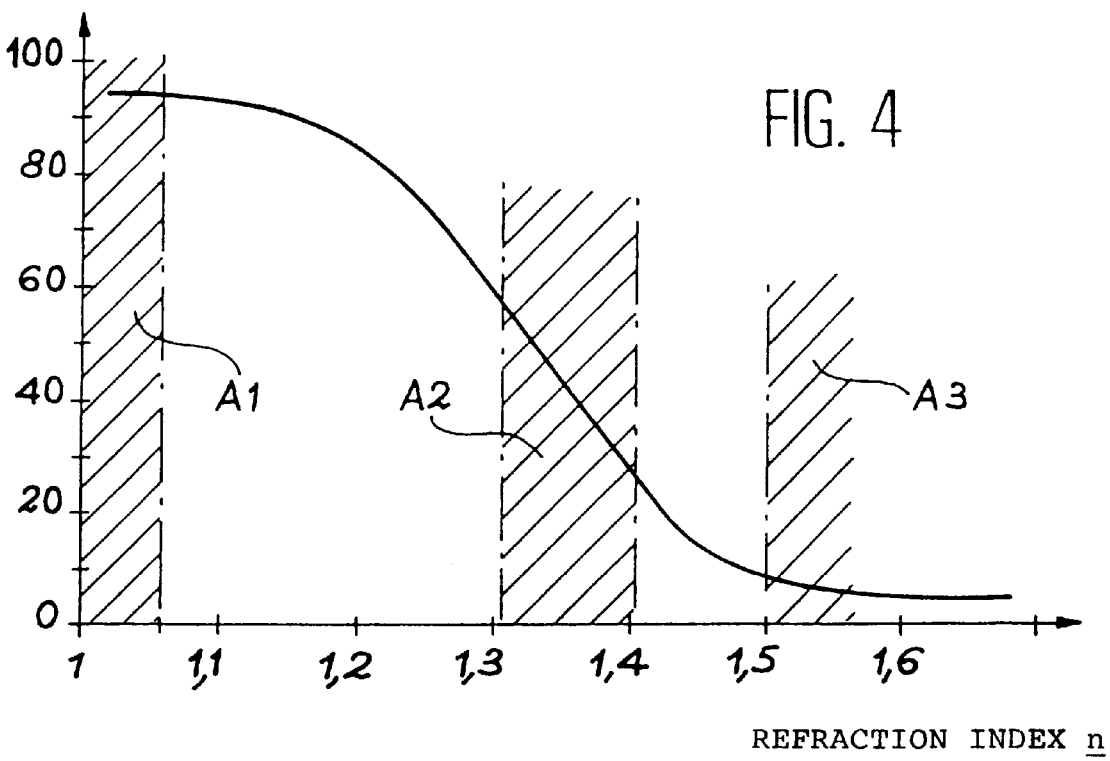
FIG. 4 shows the static response of a sapphire detector block as shown in FIG. 3, i.e. how the reflected fraction (in %) of the incident beam varies as a function of the refractive index n of the fluid in which the sensitive zone is immersed.

In particular, from the curve of FIG. 4, it can be seen that the presence of liquid oil having a refractive index that is generally close to 1.5 (zone A3) gives rise to a reflected fraction which is always less than 20%, whereas the presence of water whose refractive index lies in the range 1.3 to 1.4 (zone A2) gives rise to a reflected fraction lying in the range about 30% to about 65%. Gas is always easily distinguished because its refractive index is very close to 1 (zone A1) giving rise to a reflected fraction that is practically equal to 100%.

FIG. 2 shows a second embodiment of the detector block 10 which differs from the first described embodiment by the fact that the angles $\Theta 1$ and $\Theta 2$ formed respectively by the sensitive zone 18 and by the total reflection zone 20 relative to their common longitudinal axis 12 enable the desired angle of incidence $\Theta i$ on the sensitive zone 18 to be obtained after an incident ray such as the ray Ri travelling parallel to the axis 12 has previously struck the total reflection zone 20 and the sensitive zone 18 on a first occasion so as to be totally reflected each time, whatever the phase of the fluid in which the sensitive zone is immersed. However, when the rays reach the sensitive zone 18 for a second time they do so at the desired angle of incidence $\Theta i$ and the reflected fraction is directed towards the optical fiber parallel to the axis 12, as represented by Rr in FIG. 2.

It should be observed that as with the first embodiment shown in FIG. 1, the reverse optical path can also be followed by light rays. In other words, incident rays parallel to the axis 12 and striking the sensitive zone 18 directly, do so at the angle of incidence $\Theta i$, and the reflected fraction of said incident rays that is returned via the optical fiber parallel to the axis 12 travels subsequently successively to strike the sensitive zone 18 a second time and then to strike the total reflection zone 20 on a single occasion, with angles of incidence being such that total internal reflection of the rays is ensured in both cases, whatever the phase of the fluid in which the detector block is immersed.

When the detector block 10 is made of diamond and when the three phases of the fluid are respectively liquid oil, water, and gas, the angle of incidence $\Theta i$ may be selected to be equal to about 35° as in the first-described embodiment. In FIG. 2, the angle of incidence $\Theta i$ is 35.5°, thus causing the angle $\Theta i$ between the sensitive zone 18 and the axis 12 to be 54.5°. Given the intervening reflection of the fraction of the beam that is reflected again on the sensitive zone 18, that leads to the angle $\Theta 2$ between the total reflection zone 20 and the axis 12 being given a value of 19°.

Apparatus fitted with a detector block 10 as shown in FIG. 2 operates in a manner comparable to that of apparatus fitted with the detector block of FIG. 1. In particular, by injecting an incident light beam of non-zero divergence into the block, it is possible to distinguish between the three phases present because the fraction of the incident beam reflected by the zones 18 and 20 differs depending on whether the sensitive zone 18 is in the presence of one or another of the three phases of the fluid.

In a third embodiment of the invention shown in FIG. 3, only the portion of the incident light beam which reaches the total reflection zone 20 first is used to perform measurement. More precisely, the optical path of the rays used for performing the measurement is totally symmetrical about a plane containing the longitudinal axis 12 of the detector block 10. Thus the angles $\Theta 1$ and $\Theta 2$ formed respectively by the sensitive zone 18 and by the total reflection zone 20 relative to the axis 12 are determined so that incident rays, such as the ray Ri, which reach the total reflection zone are reflected on the sensitive zone 18 in such a manner as to reach it at the desired angle of incidence $\Theta i$. The fraction reflected by said sensitive zone is then directed along a direction normal to the axis 12 to reach the sensitive zone 18 a second time at the same angle of incidence Θi prior to being returned in part towards the total reflection zone 20 which reflects the remaining fraction of the ray parallel to the axis 12, as represented by Rr in FIG. 3.

In this embodiment, given that each ray of the beam is reflected twice on the sensitive surface 18 prior to being returned to the optical fiber, the discrimination effect on the various phases is amplified.

In an application to discriminating between the various phases of a fluid containing liquid oil, water, and gas, and when using a detector block 10 made of sapphire, this causes the angle Θi to have a value lying in the range 49° to 58°, e.g. 52°. This means that the angles Θ1 and Θ2 formed respectively by the sensitive zone 18 and the total reflection zone 20 relative to the axis 12 have values of 52° and 7°.

Apparatus fitted with a detector block 10 as shown in FIG. 3 otherwise operates in a manner analogous to that of apparatus fitted with the detector blocks shown in FIGS. 1 and 2 when an incident light beam of non-zero divergence is injected by the optical fiber having the block mounted at the end thereof.

Figure 5:
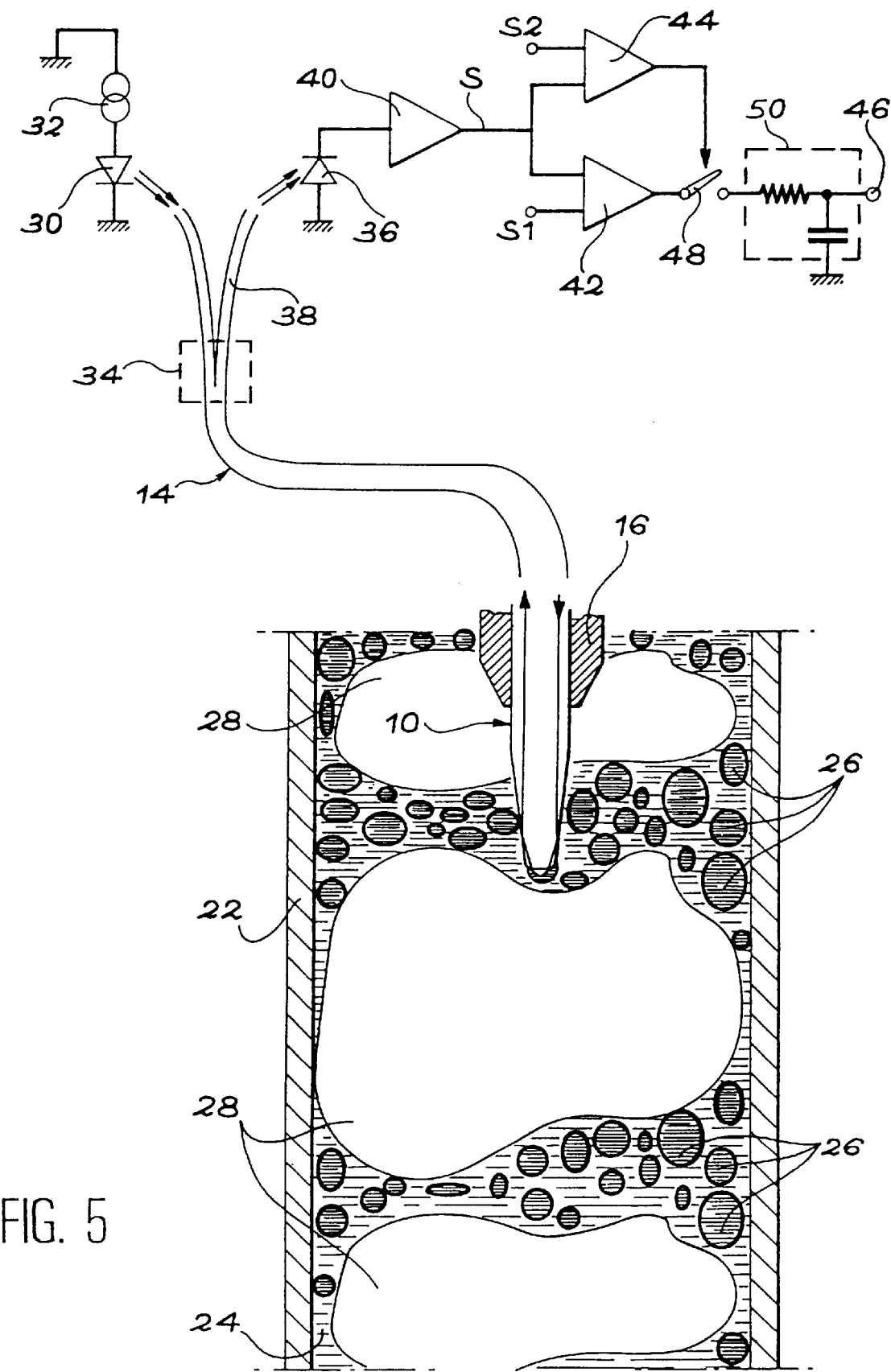
FIG. 5 is a diagram showing optical discriminator apparatus of the invention having its detector block placed in a well along which a moving three-phase fluid is flowing.

FIG. 5 is a diagram showing optical discriminator apparatus of the invention. More precisely, the apparatus is designed to provide a direct measurement of the fraction of oil present in the liquid flowing along an oil well 22.

The FIG. 5 apparatus comprises a detector block 10 placed in the moving three-phase fluid flowing along the oil well 22. The fluid contains water 24 having bubbles of oil 26 and bubbles of gas 28 therein.

By way of example, the detector block 10 may be implemented in any of the ways described above with reference to FIGS. 1 to 3. Its dimensions are deliberately exaggerated in FIG. 5.

In addition to the detector block 10, the FIG. 5 apparatus comprises both means for injecting the incident light beam into the detector block 10 and means for measuring the fraction of the incident beam as reflected by the zones 18 and 20 of the block 10.

The means for injecting the incident light beam into the detector block 10 comprise a light source constituted by a light-emitting diode (LED) 30, and the optical fiber 14. FIG. 5 also shows the current source 32 which provides electrical feed to the LED 30.

An optical coupler 34 is placed on the optical fiber 14 so as to enable it to be connected to a photodiode 36 via a second optical fiber 38. More precisely, the optical fiber 38 is connected to the optical fiber 14 by the coupler 36 in such a manner that the fraction of the incident light beam reflected on the zones 18 and 20 of the detector block 10 is directed in full towards the diode 36. This diode constitutes means for transforming the above-mentioned reflected fraction into an electrical signal whose level is representative of said fraction.

The electrical signal from the photodiode 36 passes through an amplifier 40 prior to being applied firstly to a first comparator 42 and secondly to a second comparator 44, which comparators are connected in parallel.

Figure 6:
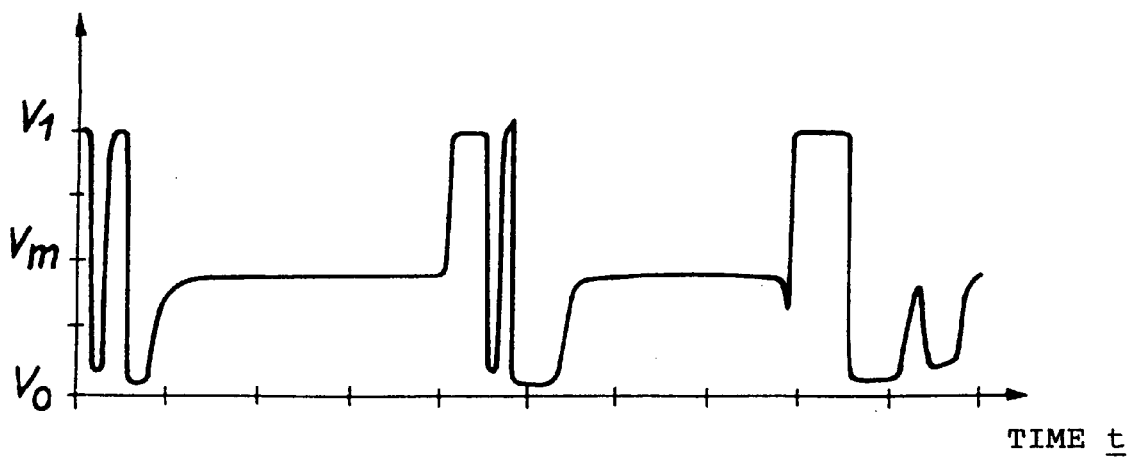
FIG. 6 shows an example of an analog signal S that may be fed to the comparators in the FIG. 5 apparatus as the phase in which the sensitive zone is immersed varies over time t.

The electrical signal from the amplifier 40 constitutes an analog signal S whose appearance is illustrated, by way of example, in FIG. 6. In particular, it can be seen in this figure that the signal S varies as a function of time t depending on the nature of the fluid phase in contact with the sensitive zone 18 of the detector block 10. Thus, the signal takes a relatively low value V0 in the presence of oil 26, a relatively high value V1 in the presence of gas 28, and a medium value Vm in the presence of water 24.

The first comparator 42 serves to transform the analog signal S into a binary signal suitable for taking up two distinct values "0" and "1" depending on whether the value of the signal S is greater than or less than a first threshold S1. More precisely, this threshold S1 is given an intermediate value between the relatively low value V0 and the medium value Vm. The first comparator 42 thus serves to detect the highest index liquid phase (oil 26) in the flow.

The second comparator 44 compares the analog signal S with a second threshold S2 whose value is intermediate between the medium value Vm and the relatively high value V1 of the signal S. Thus, the second comparator 44 likewise transforms the analog signal S into a binary signal suitable for taking on two distinct values "0" and "1" depending on whether the value of the signal S is greater than or less than the second threshold S2. This second comparator 44 thus serves to distinguish the gas phase (output "0") from the liquid phases (output "1").

The output signal from the second comparator 44 is used to control a switch 48 placed on the output path of the first comparator 42. Thus, the switch 48 is opened by the comparator 44 (output "0") whenever the signal S is greater than the second threshold S2 (i.e. in the presence of the gas phase) and it is closed by the comparator 44 (output "1") when the signal S is below the second threshold S2.

The presence of the second comparator 44 associated with the switch 48 makes it possible for the first comparator 42 to deliver a signal only when the sensitive zone of the detector block is in the presence of a liquid phase. Thus, an output signal is obtained at the output of the switch 44 which is representative of the product of the binary signals issued by the two comparators 42 and 44. The value of this output signal is thus directly representative of the relative proportions of the two liquid phases contained in the fluid, regardless of the gas fraction present therein.

In order to obtain a direct representation of the fraction of oil contained in the liquid phases of the fluid, an RC circuit 50 is placed on the output line from the first comparator 42 as seen via the switch 48. By spreading the measurement over a period of time that is sufficiently long, a signal is thus obtained that provides, with good accuracy, a direct representation of the oil fraction present in the liquid coming from the reservoir.

In the application to the oil industry, it should be observed that such a measurement can be performed both during testing of a deposit and during production from the deposit. Depending on circumstances, the measurement can be performed downhole or on the surface. Given that the measurement performed by the detector block is a local measurement, a plurality of detectors may be placed at different distances from the axis of the well and at different azimuths, so as to obtain a three-dimensional image of the phases in the effluent.

More generally, the invention makes it possible to evaluate the relative quantities of the three phases present in any three-phase fluid having two phases with refractive indices that are relatively close together and a third phase with a refractive index that is considerably smaller.

I claim:

1. A method of discriminating optically between the phases of a moving multiphase fluid capable of containing first and second phases having similar refractive indices (n1, n2) and a third phase having a refractive index (n3) that is substantially different, the method comprising the steps of:

placing, in the fluid, a sensitive zone of a detector block made of a material having a refractive index greater than the refractive indices of the three phases of the fluid; and injecting an incident light beam into the block, the divergence of the beam being such that the fraction thereof reflected by the sensitive zone is respectively strong, medium, or weak, depending on which phase is in contact with the sensitive zone.

2. A method of optically discriminating between the phases in a moving multiphase fluid that may contain water, oil, and gas, having respective refractive indices close to 1.33, 1.5, and 1, the method comprising the steps of:

placing in the fluid a sensitive zone of a detector block made of a material having a refractive index (n0) greater than 1.5; and injecting into the block an incident light beam of divergence such that the fraction reflected by the sensitive zone is respectively strong, medium, or weak, depending on the phase in contact with the sensitive zone.

3. A method of optically discriminating between the phases in a moving multiphase fluid, capable of containing first and second phases of refractive indices (n1, n2) that are similar and a third phase having a refractive index (n3) that is substantially different, the refractive indices (n1, n2, n3) decreasing from the first phase to the third phase, the method comprising the steps of:

placing in the fluid a sensitive zone and a total reflection zone that are adjacent and coaxial of a detector block made of a material having a refractive index greater than the indices of the three fluid phases, the sensitive zone and the total reflection zone forming respective first and second angles $\Theta 1$ and $\Theta 2$ relative to their common axis;

injecting into the block an incident light beam of non-zero divergence, centered on said common axis, the first and second angles $\Theta 1$ and $\Theta 2$ being such that rays of said beam that are initially parallel to the common axis strike the sensitive zone at least once at an angle of incidence $\Theta i$ intermediate between two limiting angles of reflection of the material as defined by the presence respectively of the first phase of the fluid and of the second phase of the fluid, and are reflected at least once by the total reflection zone to return in an opposite direction parallel to said common axis; and measuring a fraction of the incident beam as reflected by said zones, the relatively high, medium, or low measured value of the reflected fraction of the incident beam indicating respectively the presence of the third phase, of the second phase, and of the first phase of the fluid at the sensitive zone of the detector block.

4. A method according to claim 3, wherein a measured reflected fraction is compared with a first threshold intermediate between the medium reflected fraction and the relatively low reflected fraction, to issue continuously a first binary signal representative of the first phase; the measured reflected fraction is compared with a second threshold intermediate between the relatively high reflected fraction and the medium reflected fraction, to issue continuously a second binary signal whose zero level is representative of the third phase; and the average value of the product of the first and second binary signals is calculated, being representative of the proportion of the first phase in the first and second phases.

5. A method according to claim 3, wherein an incident light beam of non-zero divergence is injected into the detector block by connecting the detector block to an optical fiber having a non-zero numerical aperture.

6. A method according to claim 3, wherein the material of the detector block is selected from the group comprising diamond and sapphire.

7. A method according to claim 6, applied to distinguishing gas, water, and oil in a fluid, wherein a diamond detector block is used comprising a central sensitive zone and a peripheral total reflection zone which respectively form, relative to their common axis, a first angle $\Theta 1$ and a second angle $\Theta 2$ such that the reflected fraction of the incident beam is subjected to a single reflection on the sensitive zone and to a single reflection on the total reflection zone.

8. A method according to claim 6, applied to distinguishing gas, water, and oil in a fluid, wherein a diamond detector block is used comprising a central sensitive zone and a peripheral total reflection zone which respectively form, relative to their common axis, a first angle $\Theta 1$ and a second angle $\Theta 2$ such that the reflected fraction of the incident beam is subjected to a single reflection on the total reflection zone and two reflections on the sensitive zone.

9. A method according to claim 6, applied to distinguishing gas, water, and oil in a fluid, wherein a sapphire detector block is used comprising a central sensitive zone and a peripheral total reflection zone which respectively form, relative to their common axis, a first angle $\Theta 1$ and a second angle $\Theta 2$ such that the reflected fraction of the incident beam is subjected to two reflections on the total reflection zone and two reflections on the sensitive zone.

10. A method according to claim 3, wherein a detector block is used whose sensitive zone has a maximum diameter no greater than the minimum dimension of bubbles formed by the phases of the fluid.

11. Apparatus for optically discriminating between the phases of a moving multiphase fluid, the fluid being capable of containing first and second phases having similar refractive indices (n1, n2) and a third phase having a refractive index (n3) that is substantially different, the refractive indices (n1, n2, n3) decreasing from the first phase to the third phase, the apparatus comprising:

a detector block of material having a refractive index (n0) greater than the refractive indices of all three fluid phases, and including a sensitive zone; and means for injecting into the detector block an incident light beam of divergence such that the fraction reflected by the sensitive zone is respectively strong, medium, or weak, depending on which phase is in contact with the sensitive zone.

12. Apparatus for optically discriminating between the phases of a moving multiphase fluid that may contain water, oil, and gas, having respective refractive indices of about 1.33, 1.5, and 1, the apparatus comprising:

a detector block made of a material having a refractive index (n0) greater than 1.5, and including a sensitive zone; and means for injecting into the detector block an incident light beam of divergence such that the fraction reflected by the sensitive zone is respectively strong, medium, or weak, depending on which phase is in contact with the sensitive zone.

13. Apparatus for optically discriminating the phases of a moving multiphase fluid that may contain first and second phases of refractive indices (n1, n2) that are similar and a third phase having a refractive index (n3) is substantially different therefrom, the apparatus comprising:

a detector block of material having a refractive index (n0) greater than the indices of the three phases of the fluid, the block comprising a sensitive zone and a total reflection zone that are adjacent and coaxial, forming respective first and second angles $\Theta 1$ and $\Theta 2$ with their common axis;

means for injecting into the detector block an incident light beam of non-zero divergence, centered on said common axis, the first and second angles Θ1 and Θ2 being such that the rays of said beam, initially parallel to the common axis, strike the sensitive zone at least once at an angle of incidence qi that is intermediate between the two limiting reflection angles of the material as defined by the presence respectively of the first phase and of the second phase of the fluid, and is reflected at least one by the total reflection zone to return in the reverse direction parallel to said common axis; and means for measuring a fraction of the incident beam as reflected by said zones, the measured reflected fraction being respectively strong, medium, or weak, depending on whether the sensitive zone of the detector block is respectively in contact with the third phase, the second phase, or the first phase of the fluid.

14. Apparatus according to claim 13, wherein the means for measuring the reflected fraction of the incident beam comprise means for transforming said reflected fraction into electrical signals corresponding to the presence of a first second or third phase of said fluid; a first comparator for comparing the electrical signal with a first threshold (S1) intermediate between the signals emitted in the presence of the first phase and the signals emitted in the presence of the second phase, and for continuously issuing a first binary signal representative of the first phase, which signal passes through a switch; and a second comparator for comparing the electrical signal with a second threshold (S2) intermediate between the signal emitted in the presence of the third phase and the signals emitted in the presence of the first or second phases, and for continuously issuing a second binary signal that controls the switch and having a zero level representative of the third phase.

15. Apparatus according to claim 14, wherein the means for injecting an incident light beam into the detector block comprise a light source and an optical fiber of non-zero numerical aperture, connecting the light source to the detector block.

16. Apparatus according to claim 15 in combination, wherein the optical fiber includes a coupler to which a second optical fiber is connected leading to the means for transforming the reflected fraction into an electrical signal.

17. Apparatus according to claim 16, wherein the detector block is made of a material selected from the group comprising diamond and sapphire.

18. Apparatus according to claim 17, wherein the detector block is made of diamond, and comprises a central sensitive zone and a peripheral total reflection zone, the first and second angles Θ1, Θ2 being such that the reflected fraction of the incident beam is subjected to two reflections on the sensitive zone and to a single reflection on the total reflection zone.

19. Apparatus according to claim 17, wherein the detector block is made of diamond, and comprises a central sensitive zone and a peripheral total reflection zone, the first and second angles Θ1, Θ1 being such that the reflected fraction of the incident beam is subjected to single reflection on the sensitive zone and to single reflection on the total reflection zone.

20. Apparatus according to claim 17, wherein the detector block is made of sapphire, and comprises a central sensitive zone and a peripheral total reflection zone, the first and second angles Θ1, Θ2 being such that the reflected fraction of the incident beam is subjected to two reflections on the sensitive zone and to two reflections on the total reflection zone.

* * * * *